United States Patent
Kremser et al.

(10) Patent No.: US 8,187,337 B2
(45) Date of Patent: May 29, 2012

(54) TROUBLE-FREE SAFETY PROSTHESIS JOINT

(75) Inventors: Dirk Kremser, Bayreuth (DE); Hsin Fa Shen, Banqiao (TW)

(73) Assignee: Medi GmbH & Co. KG, Bayreuth (DE)

( * ) Notice: Subject to any disclaimer, the term of this patent is extended or adjusted under 35 U.S.C. 154(b) by 367 days.

(21) Appl. No.: 12/538,350

(22) Filed: Aug. 10, 2009

(65) Prior Publication Data

US 2010/0100197 A1    Apr. 22, 2010

(30) Foreign Application Priority Data

Oct. 22, 2008  (TW) ................................ 97218845 U

(51) Int. Cl.
*A61F 2/64* (2006.01)
(52) U.S. Cl. ........................................................ 623/45
(58) Field of Classification Search ............. 623/43–45, 623/FOR. 39, FOR. 43, FOR. 44, FOR. 45
See application file for complete search history.

(56) References Cited

FOREIGN PATENT DOCUMENTS

| DE | 29521138 | 8/1996 |
|---|---|---|
| DE | 20119049 | 2/2002 |
| EP | 1166726 | 1/2002 |
| JP | 2000-107212 A * | 4/2000 |

* cited by examiner

*Primary Examiner* — David H Willse
(74) *Attorney, Agent, or Firm* — Lucas & Mercanti, LLP

(57) ABSTRACT

A trouble-free safety prosthesis joint, which has a below-knee connector device with a main body, a base, a drive element and a restoring unit. The restoring unit is provided in a receiving space located in the interior of the main body and is connected to the drive element. The base extending downward from the main body serves for connection to the below-knee prosthesis. A thigh connector device is arranged on the below-knee connector device. One end of the brake element is connected to the restoring unit and the other end is connected pivotably to the thigh connector device. A brake element and a brake stirrup are also located in the receiving space of the below-knee connector device, which is connected to the thigh connector device and the brake stirrup is connected to the brake element. The brake stirrup engages the brake journal and is connected to the below-knee connector device.

13 Claims, 8 Drawing Sheets

TROUBLE-FREE SAFETY PROSTHESIS JOINT

This application claims the priority of TW 097218845 filed Oct. 22, 2008, which is incorporated by reference herein.

The invention relates to a trouble-free safety prosthesis joint, in particular to a prosthesis joint for disabled persons.

In order to improve the walking problems experienced by the disabled, prosthesis joints of various designs have been developed. The prosthesis joint acts like a knee. That is to say, the prosthesis joint is connected at the top to the thigh and at the bottom to the lower leg, the aim being for the below-knee prosthesis joint to be bent during walking in such a way that a gait is obtained that is as natural as possible. This results in improved walking flexibility.

As is shown in FIG. 1, a conventional prosthesis joint comprises a below-knee connector device 1a, a buffer device 2a, a brake device 3a and a top 4a. The brake device 3a is mounted at the rear onto a securing journal 11a arranged at the upper end of the below-knee connector device 1a. The top 4a serves for connection of the prosthesis shaft. The top 4a comprises a front arm 41a, a rear arm 42a and an adjustment device 43a. The front arm 41a is provided centrally with a transverse journal 44a which extends through the front end of the brake device 3a. The rear arm 42a is arranged pivotably on the upper end of the buffer device 2a. A gap is present between the upper end of the front side of the brake device 3a and the top 4a.

When the disabled person is standing, the thigh generates a downwardly directed force F2 [see FIG. 2], wherein the top 4a pivots about the journal 44a and thus generates an actuating moment M in the clockwise direction. A wedge piece 45a of the adjustment device 43a is pressed down against the brake device 3a, and the securing journal 11a is clamped. This avoids the prosthesis joint bending. The disabled person is therefore able to stand without any problem.

Reference is now made to FIG. 2. When a load is placed on the prosthesis joint, the journal 44a serves as rotation axis. In this way, the brake device 3a is moved slightly downward in order to generate a braking action. It is customary for the brake device 3a to be provided with a spring 31a for producing a clamping force FS, which acts as a counterforce against the braking action. When the clamping force of the spring 31a is set for normal walking, difficulties arise when walking quickly. The pivot moment increases when walking quickly, as a result of which the prosthesis joint no longer bends.

In the above-mentioned conventional prosthesis joint, there is a problem in reaching a compromise between the stability and the flexibility of the prosthesis joint. This is unsuitable in particular for intensive and rapid movement. When the physical weight is supported by the below-knee prosthesis, the top 4a is pivoted under the effect of a counteracting torque. If the torque resulting from the weight force falls below the counteracting torque, abnormal bending of the prosthesis joint may occur and the user safety may thus be impaired.

The object of the invention is to make available a trouble-free safety prosthesis joint that gives the disabled person increased and safer walking flexibility.

According to the invention, this object is achieved by a trouble-free safety prosthesis joint as described herein. Other advantageous embodiments of the invention are set forth herein.

According to the invention, a trouble-free safety prosthesis joint is provided which has:

a below-knee connector device that comprises a main body, a base, a drive element and a restoring unit, wherein a receiving space is delimited by the inner wall of the main body, and wherein the base extends from one end of the main body, and wherein the restoring unit is provided in the receiving space, and wherein one end of the restoring unit is connected to the drive element, while the other end thereof is connected pivotably to the main body;

a thigh connector device that has a connecting portion and a base portion, wherein the connecting portion is provided at one end with a thigh locking element, while the base portion is arranged at another end of the connecting portion, and wherein the restoring unit is secured on one end of the drive element, while the base portion is arranged pivotably on the other end thereof;

a brake element which is provided in the receiving space and is secured on the thigh connector device;

a brake stirrup which is located in the receiving space, wherein the brake stirrup has a first journal hole and a first securing portion, and wherein the first securing portion is provided with a third locking hole which is connected to the brake element; and a brake journal which extends through the journal hole and is secured on the below-knee connector device.

In summary, the following advantages, for example, can be obtained using the trouble-free safety prosthesis joint according to the invention:

1. When the mass center of gravity of the disabled person is located behind the trouble-free safety prosthesis joint, the brake element bears on the brake stirrup such that the peripheral surface of the first journal hole is pressed against the outer wall of the brake journal. In this way, no abnormal bending of the prosthesis joint takes place. Safe use is thereby ensured.

2. When the mass center of gravity of the disabled person is located in front of the trouble-free safety prosthesis joint, the brake stirrup is pivotably about the brake journal. Trouble-free use is thereby ensured. Moreover, the disabled person is provided with increased walking flexibility.

The invention and embodiments thereof are explained in greater detail below with reference to the drawing, in which.

Figure 1:
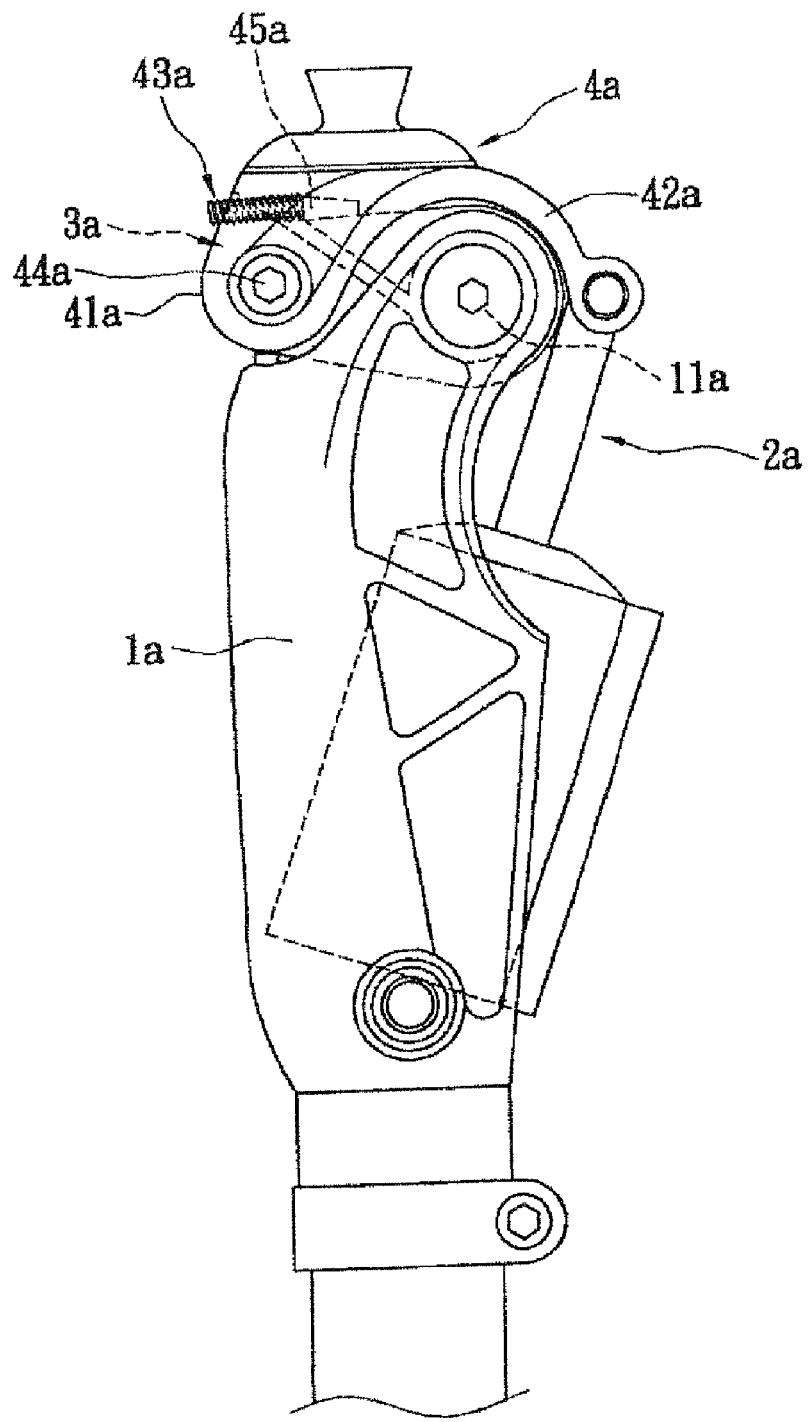
FIG. 1 shows a side view of a conventional prosthesis joint.
Figure 2:
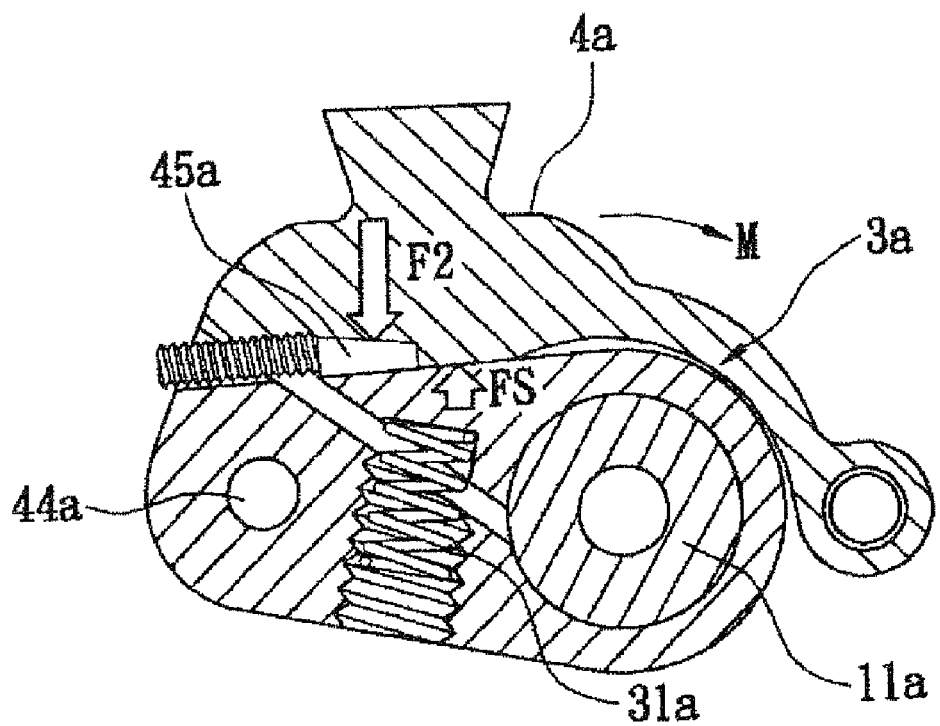
FIG. 2 shows a schematic view of the effect of the force of a pressure device of the conventional prosthesis joint.
Figure 3:
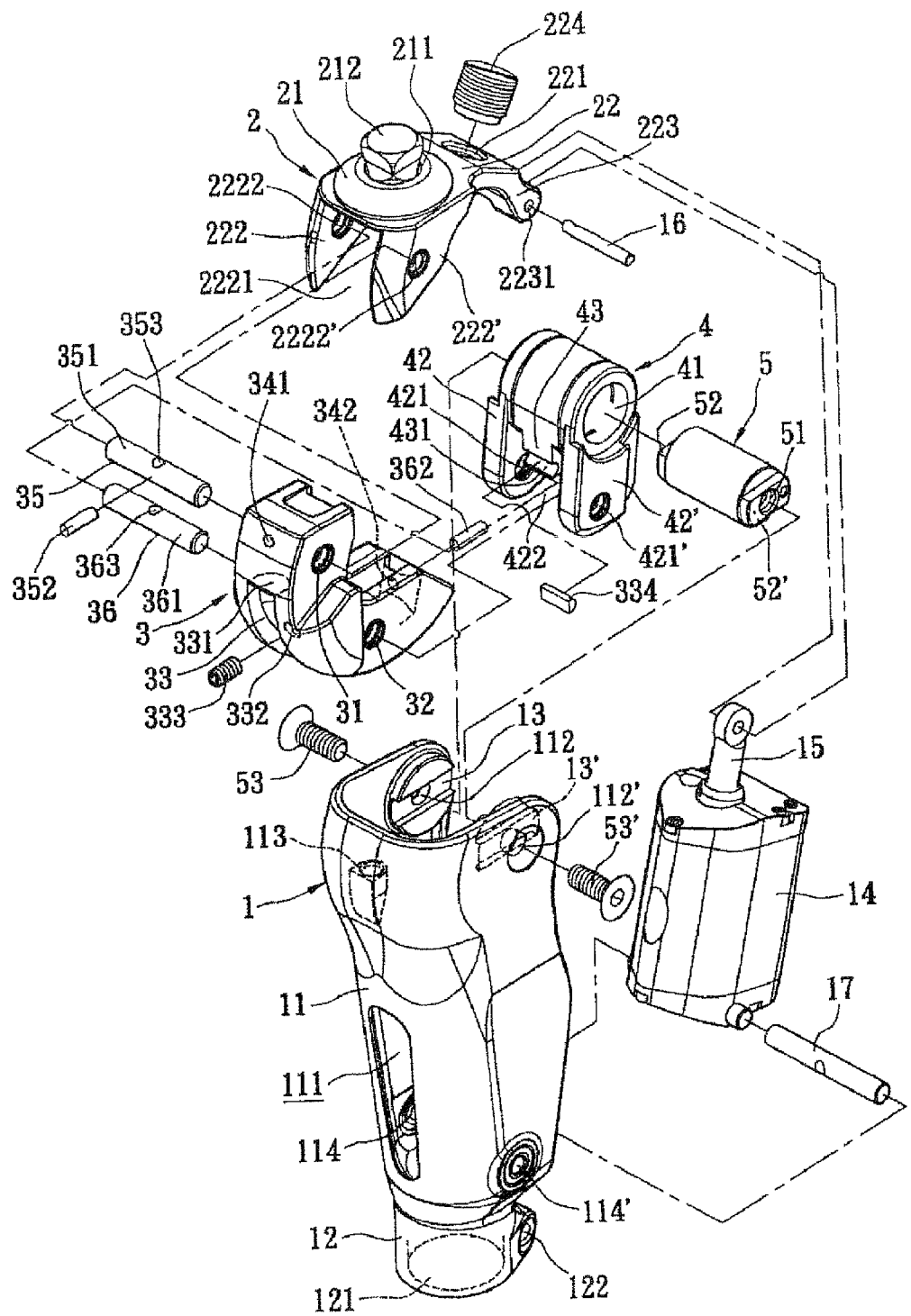
FIG. 3 shows a perspective exploded view of a prosthesis joint according to the invention.
Figure 4:
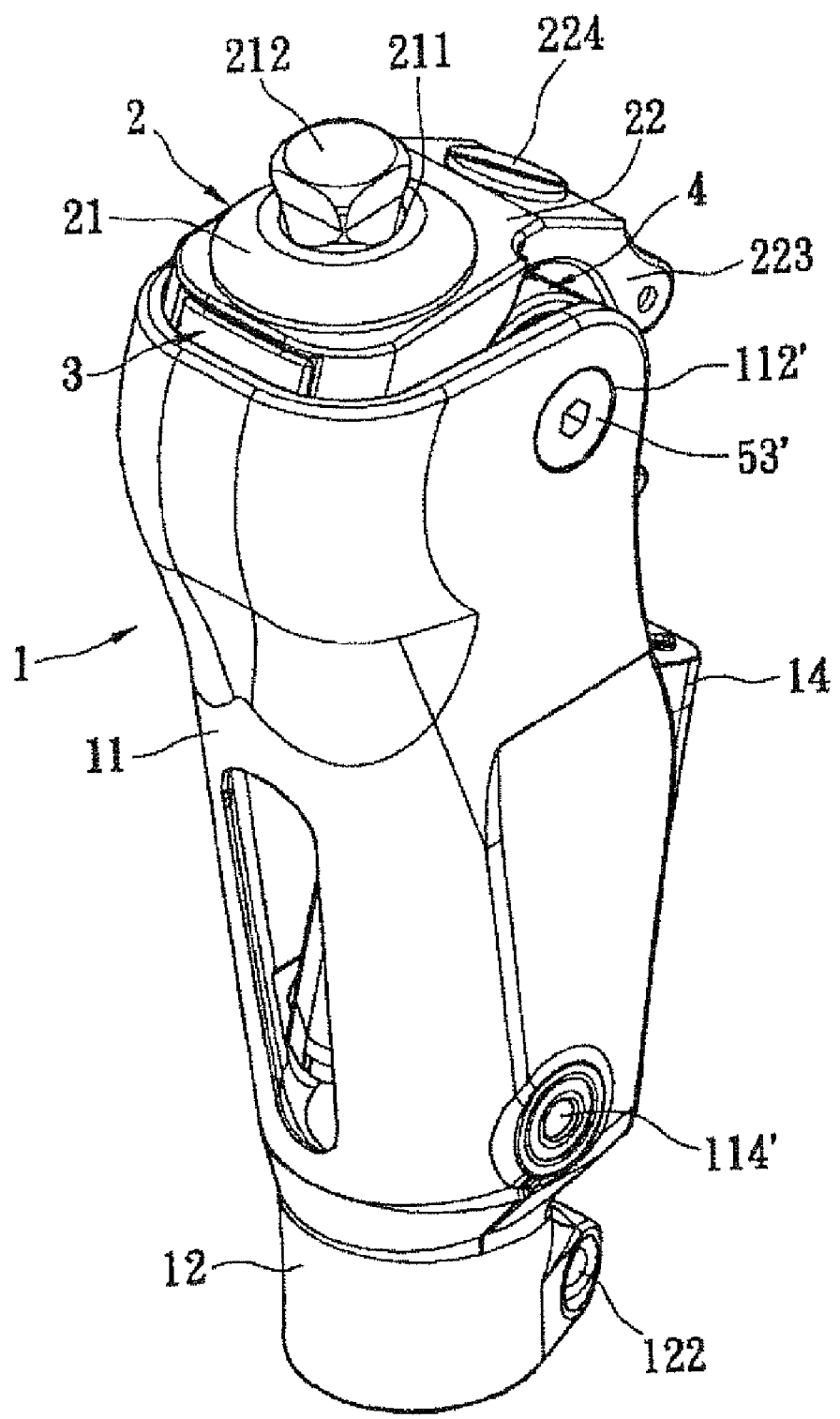
FIG. 4 shows a perspective assembled view of a prosthesis joint according to the invention.

Referring to FIG. 3 to FIG. 4, a trouble-free safety prosthesis joint according to the invention has a below-knee connector device 1, a thigh connector device 2, a brake element 3, a brake stirrup 4 and a brake journal 5.

The below-knee connector device 1 has a substantially U-shaped, thin main body 11, wherein the base 12 extends from one end of the main body 11. The base 12 has a below-knee securing opening 121 and a below-knee locking groove 122. The below-knee securing opening 121 serves to receive a below-knee prosthesis which can be locked with the below-knee locking groove 122 on the below-knee connector device 1. A receiving space 111 is delimited by the inner wall of the main body 11, wherein a restoring unit 14 can be received in the receiving space 111. The restoring unit 14 can be designed as a restoring spring. Alternatively, it can be designed as a piston unit which is composed of a cylinder, a pressure piston and a bottom adjustment cap. The restoring unit 14 is connected at the top to a drive element 15. The main body 11 is provided at the top, on both sides, with a pair of mutually facing second journal holes 112, 112' and with a pair of positioning slits 13, 13', wherein the positioning slits 13, 13' are adapted to the second journal holes 112, 112'. The main body 11 is provided at the bottom, on both sides, with a pair of mutually facing third journal holes 114, 114'. The restoring unit 14 is arranged pivotably on a second rotary journal 17 inserted into the third journal holes 114, 114'. The main body 11 is provided on its inner wall with an abutment projection 113.

The thigh connector device 2 has a connecting portion 21 which is provided at the top with a first threaded hole 211. A thigh locking element 212 can be screwed into the first threaded hole 211, wherein the thigh locking element 212 is connected to the thigh. Extending from the bottom surface of the connecting portion 21, there is a base portion 22 which is provided with a first threaded adjustment hole 221 into which a first threaded adjustment bolt 224 can be screwed. The first threaded adjustment bolt 224 is made internally of elastic material. The shock-absorbing effect is obtained when the bottom surface of the first threaded adjustment bolt 224 comes into contact with the peripheral surface of the brake stirrup 4 as a result of a movement-induced pivoting of the thigh connector element 2 relative to the brake stirrup 4. From both sides of one end of the base portion 22 there extends in each case a second securing portion 222, 222'. A connecting portion 223 is formed at another end of the base portion 22. A first receiving groove 2221 is delimited by the second securing portions 222, 222' and the base portion 22. The securing portions 222, 222' each have a fourth locking hole 2222 and 2222', respectively. The connecting portion 223 has a connecting hole 2231 which is connected pivotably to the other end of the drive element 15 via a first rotary journal 16.

The brake element 3 is provided in the receiving space 111. Moreover, the brake element 3 has a first locking hole 31, a second locking hole 32, a first locking element 35 and a second locking element 36. The first and second locking elements 35, 36 engage in the first and second locking holes 31, 32, respectively. The first locking element 35 comprises a first rotary pin 351 and a first threaded pin 352, while the second locking element 36 has a second rotary pin 361 and a second threaded pin 362. The brake element 3 is provided with a slide track 33 which comprises a second threaded adjustment hole 332. Moreover, the slide track 33 has an abutment surface 331. A second threaded adjustment bolt 333 can be screwed into the second threaded adjustment hole 332 and comes into contact with a bearing element 334.

The brake stirrup 4 is located in the receiving space 111 and has a first journal hole 41. Extending from both sides of the first journal hole 41 there is in each case a first securing portion 42, 42'. A second receiving groove 422 is delimited by the two securing portions 42, 42' and by the first journal hole 41. The securing portions 42, 42' each have a third locking hole 421 and 421', respectively. On the outer peripheral surface of the first journal hole 41 there is a bearing portion 43, which is provided in the second receiving groove 422. The bearing portion 43 has a bearing groove 431 in which a bearing element 334 can be received.

The brake journal 5 is inserted into the first journal hole 41 of the brake stirrup 4. Both ends of the brake journal 5 are provided with positioning portions 52, 52', respectively. The two positioning portions 52, 52' are adapted in size and shape to the positioning slits 13, 13' of the below-knee connector device 1. The two positioning portions 52, 52' are provided with a second threaded hole 51 which extends through both ends of the brake journal 5.

Upon assembly, the brake journal 5 is inserted into the first journal hole 41 of the brake stirrup 4. Thereafter, a pair of threaded rods 53, 53' (screws) are inserted through the second journal holes 112, 112' and into the second threaded hole 51 of the brake journal 5. In this way, the brake journal 5 is secured to the below-knee connector device 1. Moreover, the brake stirrup 4 can be pivoted relative to the brake journal 5. An end of the brake element 3 is then fitted into the second receiving groove 422 of the brake stirrup 4 in such a way that the brake element 3 bears against the bearing portion 43 of the brake stirrup 4. The second rotary pin 361 is guided through the third locking hole 421, 421' of the brake stirrup 4 and through the second locking hole 32 of the brake element 3, while the second threaded pin 362 extends through a fourth threaded hole 342 of the brake element 3 and engages in a second groove 363 of the second rotary pin 361. The other end of the brake element 3 is fitted into the first receiving groove 2221 of the thigh connector device 2, wherein the first rotary pin 351 is guided through the fourth locking hole 2222, 2222' of the thigh connector device 2 and through the first locking hole 31 of the brake element 3. Moreover, the first threaded pin 352 extends through a third threaded hole 341 of the brake element 3 and engages in a first groove 353 of the first rotary pin 351.

One end of the drive element 15 is pivotably connected to the connecting portion 223 of the thigh connector device 2, while the other end is connected to the restoring unit 14. The restoring unit 14 is accommodated in the receiving space 111 of the below-knee connector device 1 and is arranged pivotably on the below-knee connector device 1. When the prosthesis joint is bent, the restoring unit 14 provides a restoring force with which the below-knee prosthesis returns to its starting position.

Figure 5:
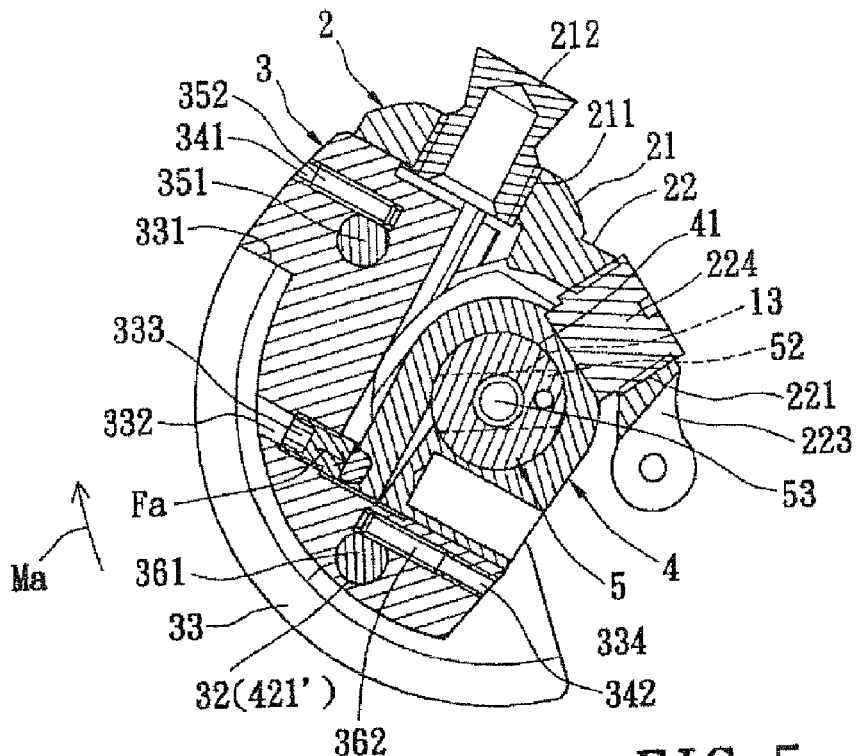
FIG. 5 shows a schematic view of the effect of the force of a brake element and of a brake stirrup of the prosthesis joint according to the invention.

Reference is made below to FIG. 5. When the mass center of gravity of the disabled person is located behind the prosthesis joint, the body weight relative to the brake journal 5 generates a torque Ma in the clockwise direction, as a result of which the second threaded adjustment bolt 333 of the brake element 3 bears against the bearing element 334 located in the bearing groove 431 of the brake stirrup 4 and thus generates a contact force Fa. Application of the torque Ma then results in a rotation of the brake element 3 about the rotary pin 361 and therefore a movement of the brake element relative to the brake stirrup 4, such that, as a result of the position of the rotary pin below the threaded adjustment bolt 333, the latter is pressed against the bearing element 334, as a result of which the contact force Fa is in turn generated. With the contact force Fa, the peripheral surface of the first journal hole 41 can press against the outer wall of the brake journal 5. This avoids the brake stirrup 4 pivoting around the brake journal 5. One side of the bearing element 334 is flat and serves for contact with the second threaded adjustment bolt 333, while the other side has a semicircular design that comes into contact with the bearing groove 431. In this way, the contact force Fa can act uniformly on the brake stirrup 4 in such a way that the peripheral surface of the first journal hole 41 is pressed against the outer wall of the brake journal 5. Moreover, the contact tension of the second threaded adjustment bolt 333 with the bearing element 334 is adjustable, such that the peripheral surface of the first journal hole 41 can be pressed even more strongly against the outer wall of the brake journal 5. In addition, wear occurs on the bearing element 334 only with difficulty, as a result of which an increased lifetime of the prosthesis joint can be achieved.

Before or at the same time as the brake element 3 is pivoted about the rotary pin 361 relative to the brake stirrup 4, there is another relative movement. On account of the applied torque Ma, the thigh connector device 2 also pivots about the rotary journal 351, such that there is a movement of the thigh connector element 2 relative to the brake element 3, but also relative to the brake stirrup 4. The threaded adjustment bolt 224 is pressed against the brake stirrup. The elastic, damping property of the threaded adjustment bolt results in a damped movement. That is to say, when the joint is loaded and a torque directed in the clockwise direction is built up, two rotation movements take place, namely a first rotation of the thigh connector element 2 around the rotary pin 351 relative to the brake element 3 (wherein this movement is damped if a damping threaded adjustment bolt is provided, which does not necessarily have to be the case), and a second rotation of the brake element 3 about the rotary pin 361 relative to the brake stirrup 4, which results in the brake journal 5 being wedged in the brake stirrup 4, i.e. blocking of the joint.

Figure 6:
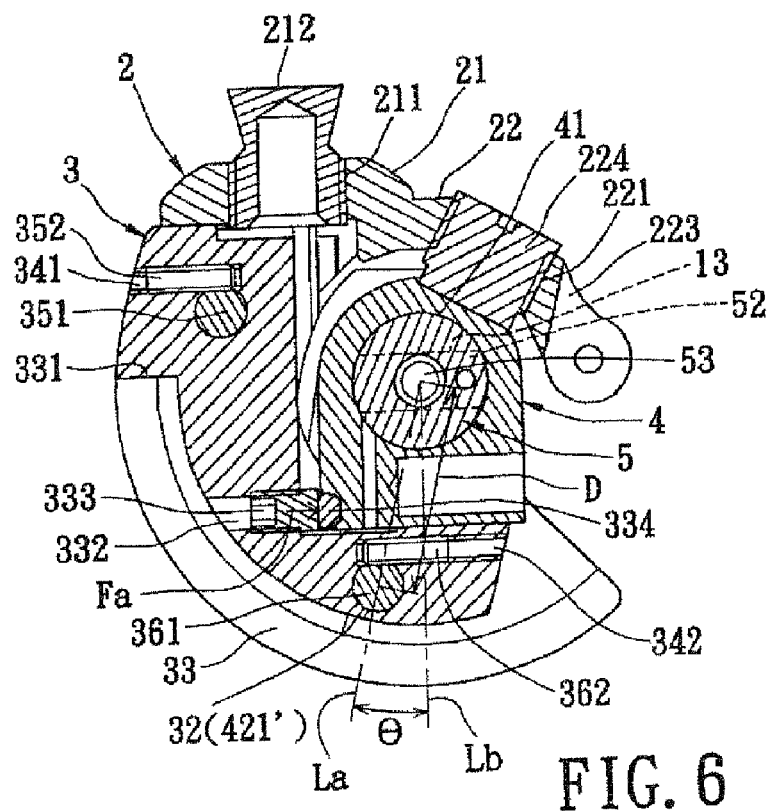
FIG. 6 shows a section through the brake element and the brake stirrup of the prosthesis joint according to the invention in a trouble-free state.
Figure 7:
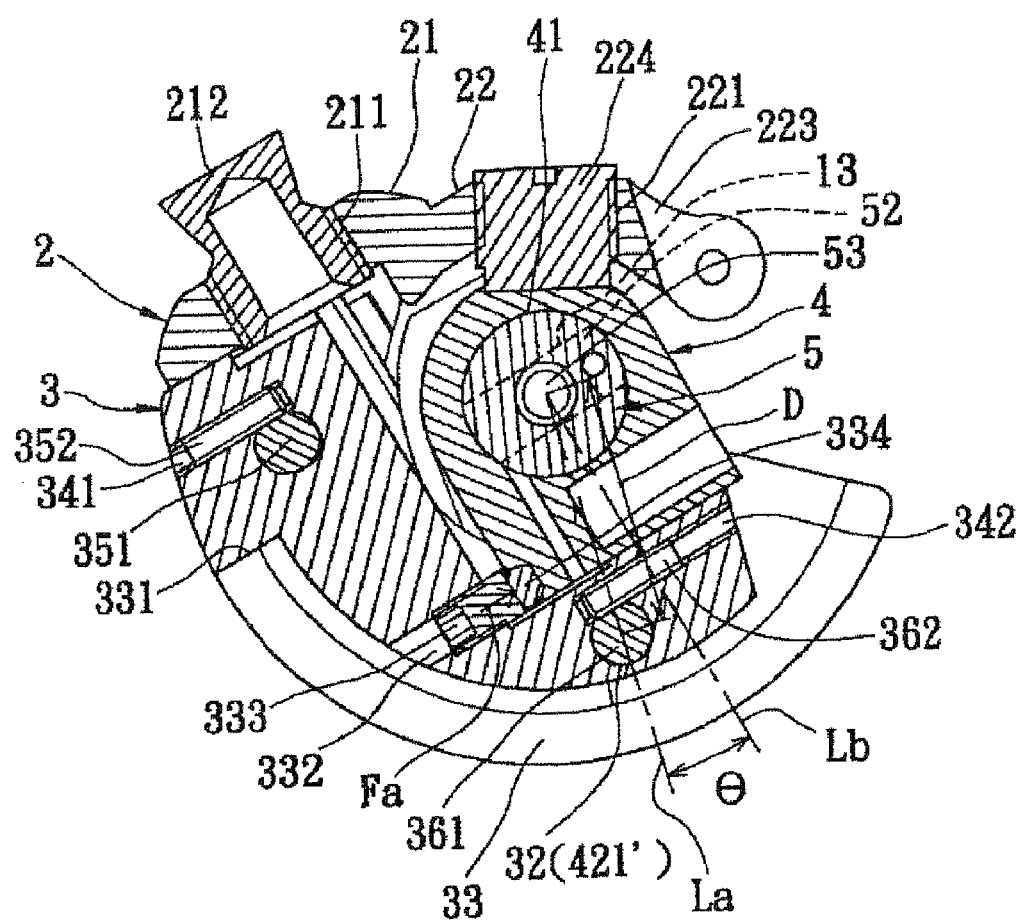
FIG. 7 shows a section through the brake element and the brake stirrup of the prosthesis joint according to the invention in another trouble-free state.

Reference is now made to FIG. 6 and FIG. 7. When the mass center of gravity of the disabled person is located in front of the prosthesis joint, the body weight relative to the brake journal 5 does not generate any torque, as a result of which the brake stirrup 4 is pivotable about the brake journal 5. Moreover, no disturbance occurs, and this gives the disabled person increased walking flexibility. The angle θ between the connecting line La, formed by the center point of the third locking hole 421, 421' and the center point of the journal hole 41, and the perpendicular line Lb of the center point of the first journal hole 41, and the distance D between the center point of the third locking hole 421, 421' and the center point of the first journal hole 41, are therefore in relation as the peripheral surface of the first journal hole 41 is pressed against the outer wall of the brake journal 5. In the illustrative embodiment shown, the angle θ is in the range of 15° to 25°. The greater the distance D, the better the effect of the pressure of the peripheral surface of the first journal hole 41 against the outer wall of the brake journal 5.

When the disabled person takes a step, the mass center of gravity of the disabled person is located behind the prosthesis joint [see FIG. 5]. The peripheral surface of the first journal hole 41 is now pressed against the outer wall of the brake journal 5. This ensures that the brake stirrup 4 does not pivot about the brake journal 5 until the foot comes into contact with the ground and the body is moved forward. In the period between the time when the mass center of gravity of the disabled person is located in front of the prosthesis joint [see FIG. 6] and the time when the front of the foot is lifted from the ground [see FIG. 7], the brake stirrup 4 can be pivoted about the brake journal 5. In this way, no abnormal bending of the prosthesis joint occurs in the period between the time when the disabled person takes a step and the time when the foot comes into contact with the ground and the mass center of gravity of the disabled person is moved in front of the prosthesis joint. Safe use is thereby ensured. Moreover, in the period between the time when the body of the disabled person is moved forward and the time when said person takes the next step, the prosthesis joint can be freely angled and pivoted. This results in a smooth walking movement.

Figure 8:
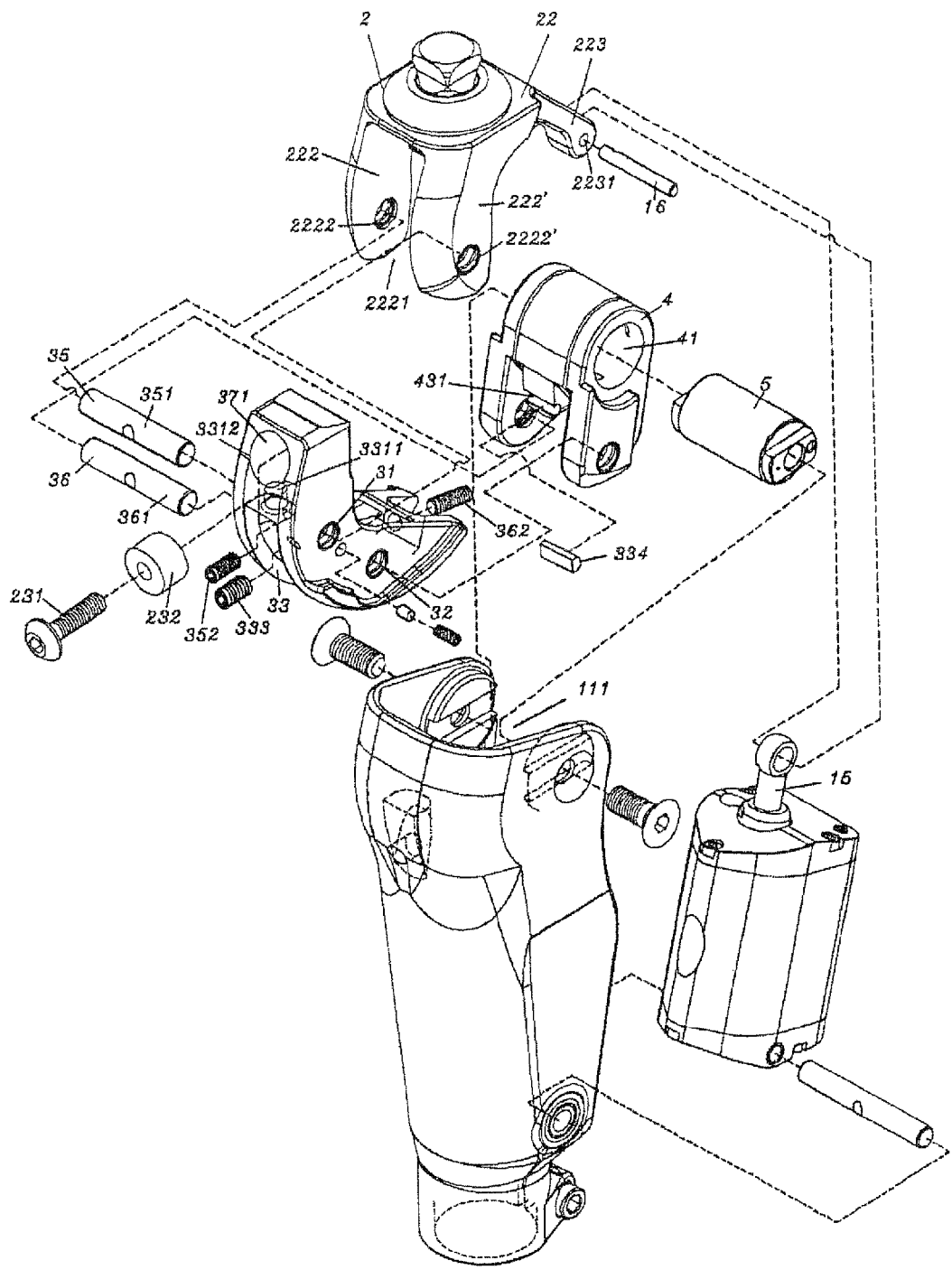
FIG. 8 shows a perspective exploded view of another illustrative embodiment of a prosthesis joint according to the invention.
Figure 9:
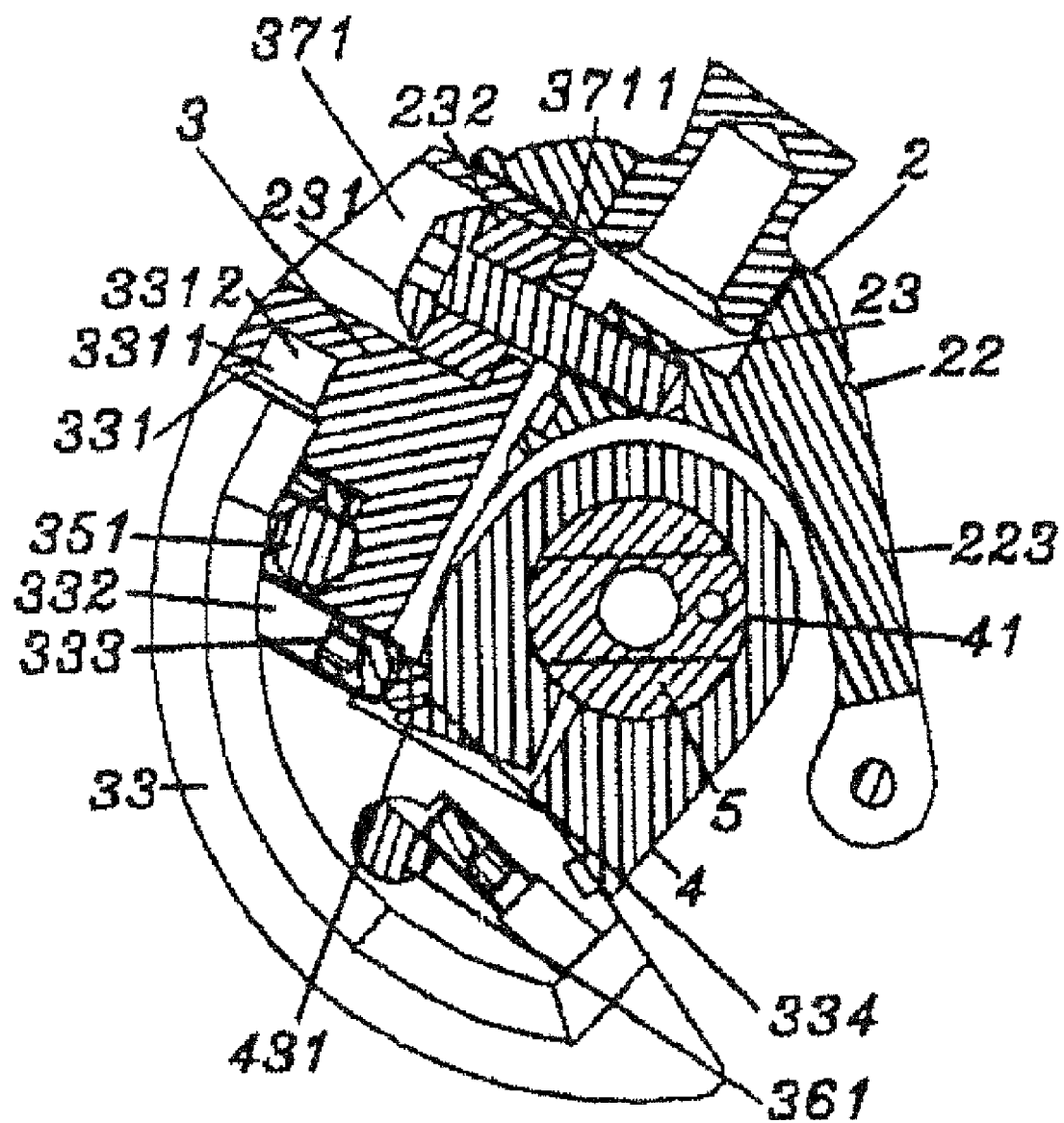
FIG. 9 shows a schematic view of the effect of the force of a brake element and of a brake stirrup of the other illustrative embodiment of a prosthesis joint according to the invention in FIG. 8.

FIGS. 8 and 9 show a second embodiment of a prosthesis joint according to the invention. The thigh connector device 2 has a base portion 22. Below the base portion there is a threaded hole 23 into which an adjustable clamping screw 231 can be screwed. The adjustable clamping screw 231 secures an elastic buffer 232 whose underside comes into contact with the brake element 3. The buffer 232 is exchangeable, such that a buffer can easily be fitted which is adapted in terms of its hardness and its damping behavior to the actual requirements arising during wearing of the prosthesis. Upon contact of the elastic buffer 232 with the brake element 3, or upon pivoting of the thigh connector device 2 about the rotary pin 351, the tilting of the adjustable clamping screw 231, which is moved with the thigh connector device 2 because it is firmly screwed therein, leads to a deformation of the buffer 232 and thereby to a damping action.

Extending from both sides of one end of the base portion 22, there is in each case a second securing portion 222, 222'. A connecting portion 223 is formed at another end of the base portion 22. A first receiving groove 2221 is delimited by the second securing portions 222, 222' and the base portion 22. The securing portions 222, 222' each have locking holes 2222, 2222', respectively. The connecting portion 223 has a connecting hole 2231 which is pivotably connected to the other end of the drive element 15 via a first rotary journal 16.

The brake element 3 is provided in the receiving space 111. Moreover, the brake element 3 has a first locking hole 31, a second locking hole 32, a first locking element 35 and a second locking element 36. The first and second locking elements 35, 36 engage in the first and second locking holes 31, 32, respectively. The first locking element 35 comprises a first rotary pin 351 and a first threaded pin 352, while the second locking element 36 has a second rotary pin 361 and a second threaded pin 362. The brake element 3 is provided with a slide track 33 which comprises a second threaded adjustment hole 332. Moreover, the slide track 33 has an abutment surface 331. The abutment surface 331 has a bore 3311, and an elastic body 3312 is fixed in this bore 3311. Above the abutment surface 331 of the slide track 33, a cavity is formed, if appropriate with a bulge 371 on the bottom side, for the adjustable clamping screw 231 and the elastic buffer 232. Only the bottom or the bearing surface 3711 of the optionally provided bulge 371 touches the elastic buffer 232. A second threaded adjustment bolt 333 can be screwed into the second threaded adjustment hole 332 and comes into contact with a bearing element 334.

Reference is now made to FIG. 9. When the mass center of gravity of the disabled person is located behind the prosthesis joint, the body weight relative to the brake journal 5 generates a torque Ma in the clockwise direction. In this way, the thigh connector device 2 pivots about the first rotary pin 351. The movement is damped and limited by the elastic buffer 232 bearing on the brake element 3, since the adjustable screw 231 extends through the buffer 232 and deforms the latter during the pivoting, such that the buffer builds up a restoring force that damps the pivoting movement. The brake element 3 then pivots about the second rotary pin 361, as a result of which the second threaded adjustment bolt 333 of the brake element 3 bears against the bearing element 334 located in the bearing groove 431 of the brake stirrup 4 and thereby generates a contact force Fa. This is because application of the torque Ma results in a rotation of the brake element 3 about the rotary pin 361 and therefore a movement of the brake element relative to the brake stirrup 4, such that, as a result of the position of the rotary pin below the threaded adjustment bolt 333, the latter is pressed against the bearing element 334, as a result of which the contact force Fa is in turn generated. With the contact force Fa, the peripheral surface of the first journal hole 41 can press against the outer wall of the brake journal 5. This avoids the brake stirrup 4 pivoting about the brake journal 5.

When the below-knee connector device is moved from an angled position to the starting position, the abutment projection 113 is guided in the semicircular slide track 33 until the movement is arrested by the abutment projection 113 abutting against the abutment surface 331. This abutment action is damped by the elastic body 3312 against which the abutment projection 113 runs.

The invention and the two embodiments are mainly distinguished by the fact that, as a result of the pivot bearing of the thigh connector device 2 on the brake element and the pivot bearing of the brake stirrup 4 on the brake element, two separate rotation movements are possible, namely a pivoting of the thigh connector device 2 relative to the brake element 3, which pivoting movement can be damped by any damping element present (224 or 232), and a pivoting of the brake element 3 relative to the brake stirrup 4, which movement leads to the brake journal 5 being wedged in the brake stirrup 4 and thus to the joint being locked.

Although the invention has been described with reference to two examples that are presently regarded as the most practicable and preferred embodiments, it will be appreciated that the invention is not limited to the disclosed illustrative embodiments. On the contrary, the invention is intended to cover various modifications and similar arrangements whose features lie within the scope of protection of the appended claims.

List of Reference Signs
1*a* below-knee connector device
11*a* securing journal
2*a* buffer device
3*a* brake device
31*a* spring
4*a* top
41*a* front arm
42*a* rear arm
43*a* adjustment device
44*a* journal
45*a* wedge piece
F2 downwardly directed force
M actuating moment
FS clamping force
1 below-knee connector device
11 main body
111 receiving space
112 second journal hole
112' second journal hole
113 abutment projection
114 third journal hole
114' third journal hole
12 base
121 below-knee securing opening
122 below-knee locking groove
13 positioning slit
13' positioning slit
14 restoring unit
15 drive element
16 first rotary journal
17 second rotary journal
2 thigh connector device
21 connecting portion
211 first threaded hole
212 thigh locking element
22 base portion
221 first threaded adjustment hole
222 second securing portion
222' second securing portion
2221 first receiving groove
2222 fourth locking hole
2222' fourth locking hole
223 connecting portion
2231 connecting hole
224 first threaded adjustment bolt
23 threaded hole
231 adjustable clamping screw
232 elastic buffer
3 brake element
31 first locking hole
32 second locking hole
33 slide track
331 abutment surface
3311 bore in abutment surface
3312 elastic body
332 second threaded adjustment hole
333 second threaded adjustment bolt
334 bearing element
341 third threaded hole
342 fourth threaded hole
35 first locking element
351 first rotary pin
352 first threaded pin
353 first groove
36 second rotary pin
361 second rotary pin
362 second threaded pin
363 second groove
371 bulge
3711 bearing surface
4 brake stirrup
41 first journal hole
42 securing portion
42' securing portion
421 third locking hole
421' third locking hole
422 second receiving groove
43 bearing portion
431 bearing groove
5 brake journal
51 second threaded hole
52 positioning portion
52' positioning portion
53 threaded rod
53' threaded rod
Ma torque
Fa contact force
La connecting line
Lb perpendicular line
angle
D distance

The invention claimed is:

1. A trouble-free safety prosthesis joint, comprising:
a below-knee connector device having a main body, a base, a drive element and a restoring unit, a receiving space is delimited by an inner wall of the main body, and the base extends from one end of the main body, and wherein the restoring unit is provided in the receiving space, and one end of the restoring unit is connected to the drive element, while the other end thereof is connected pivotably to the main body;
a thigh connector device having a connecting portion and a base portion, the connecting portion is provided at one end with a thigh locking element, while the base portion is arranged at another end of the connecting portion, and the restoring unit is secured on one end of the drive element, while the base portion is arranged pivotably on the other end of the drive element;

a brake element provided in the receiving space and pivotably connected to the thigh connector device;

a brake stirrup which is located in the receiving space, having a first journal hole and a first securing portion the first securing portion is provided with a third locking hole which is pivotably connected to the brake element; and a brake journal which extends through the journal hole and is secured on the below-knee connector device.

2. The trouble-free safety prosthesis joint of claim 1, wherein the base portion has a first threaded adjustment hole into which a first threaded adjustment bolt can be screwed, and the first threaded adjustment bolt comes into contact with the brake stirrup.

3. The trouble-free safety prosthesis joint of claim 2, wherein the threaded adjustment bolt is made partly of an elastic shock-absorbing material.

4. The trouble-free safety prosthesis joint of claim 1, wherein below the base portion there is a threaded hole into which an adjustable clamping screw extending through the brake element is screwed, via which adjustable clamping screw an elastic buffer is fixed on the brake element.

5. The trouble-free safety prosthesis joint of claim 4, wherein the brake element has a cavity whose bottom has a bulge, into which the buffer is fitted and is pressed against the bottom of the cavity, via the adjustable clamping screw screwed into the threaded hole of the base portion.

6. The trouble-free safety prosthesis joint of claim 5, wherein the pivoting movement of the thigh connector device relative to the brake element is damped via the buffer, and the pivoting movement of the brake stirrup relative to the brake element leads to the brake journal being wedged in the journal hole.

7. The trouble-free safety prosthesis joint of claim 1, wherein the brake stirrup has a bearing groove in which a bearing element is received, and the brake element has a second adjustable threaded bolt that bears against the bearing element.

8. The trouble-free safety prosthesis joint of claim 7, wherein one side of the bearing element is flat, while the other side thereof is designed as a semicircle.

9. The trouble-free safety prosthesis of claim 1, wherein a second securing portion extends from the base portion, and one end of the second securing portion has a first receiving groove, while a first securing portion has a second receiving groove, and one end of the brake element is provided in the first receiving groove, while the other end of the brake element is located in the second receiving groove.

10. The trouble-free safety prosthesis joint of claim 9, wherein a rotary pin, via which the thigh connector device is connected pivotably to the brake element, extends through a fourth locking hole provided in the second securing portion and through a first locking hole provided at the end of the brake element received in the receiving groove, and in that a rotary pin, via which the securing stirrup is pivotably connected to the brake element, extends through a third locking hole in the first securing portion and through a second locking hole provided at the end of the brake element received in the receiving groove.

11. The trouble-free safety prosthesis joint of claim 1, wherein the brake element has a slide track, and the main body is provided on its inner face with an abutment projection which can be received in the slide track, and an abutment surface is formed at one and of the slide track, and the abutment projection abuts against the abutment surface.

12. The trouble-free safety prosthesis joint of claim 11, wherein the abutment surface has a bore in which an elastic body is received that damps the abutment of the abutment projection.

13. The trouble-free safety prosthesis joint of claim 1, wherein a connecting line formed from a center point of the third locking hole provided on the brake stirrup and the center point of the journal hole provided on the brake stirrup is at an angle of 15° to 25° to a perpendicular line of the center point of the first journal hole.

\* \* \* \* \*